United States Patent
Gillespie et al.

(10) Patent No.: US 11,731,926 B2
(45) Date of Patent: Aug. 22, 2023

(54) PROCESS FOR PURIFICATION OF PRODUCTS

(71) Applicant: LanzaTech, Inc., Skokie, IL (US)

(72) Inventors: Ralph Gillespie, Skokie, IL (US);
Michelle Kocal, Skokie, IL (US);
Wyatt Eric Allen, Skokie, IL (US);
Richard R Rosin, Skokie, IL (US);
Donovan Tran, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 349 days.

(21) Appl. No.: 17/183,204

(22) Filed: Feb. 23, 2021

(65) Prior Publication Data

US 2021/0284592 A1 Sep. 16, 2021

Related U.S. Application Data

(60) Provisional application No. 62/988,176, filed on Mar. 11, 2020.

(51) Int. Cl.

| | | |
|---|---|---|
| *C07C 29/84* | (2006.01) | |
| *C07C 29/88* | (2006.01) | |
| *B01D 3/00* | (2006.01) | |
| *B01D 3/14* | (2006.01) | |
| *C07C 29/76* | (2006.01) | |
| *B01D 15/36* | (2006.01) | |
| *C12P 7/06* | (2006.01) | |

(52) U.S. Cl.
CPC .............. *C07C 29/84* (2013.01); *B01D 3/002* (2013.01); *B01D 3/143* (2013.01); *B01D 15/362* (2013.01); *C07C 29/76* (2013.01); *C07C 29/88* (2013.01); *C12P 7/06* (2013.01)

(58) Field of Classification Search
CPC ......... C07C 29/84; C07C 29/88; B01D 3/002; B01D 3/14
See application file for complete search history.

(56) References Cited

U.S. PATENT DOCUMENTS

| | | |
|---|---|---|
| 4,760,204 A | 7/1988 | Osterburg et al. |
| 5,800,681 A | 9/1998 | Berg |
| 8,980,596 B2 | 3/2015 | Schultz |
| 10,252,183 B2 | 4/2019 | Schultz |
| 2010/0196979 A1 | 8/2010 | Birkmire |
| 2010/0304455 A1 | 12/2010 | Inoue |
| 2012/0115200 A1 | 5/2012 | Dottori |
| 2017/0225098 A1 | 8/2017 | Schultz |
| 2018/0264375 A1 | 9/2018 | Sechrist et al. |
| 2020/0255362 A1 | 8/2020 | Gao et al. |

FOREIGN PATENT DOCUMENTS

| | | |
|---|---|---|
| CN | 103119011 A | 5/2013 |
| CN | 105189765 A | 12/2015 |
| CN | 110760548 A | 2/2020 |

OTHER PUBLICATIONS

International Search Report and Written Opinion, issued in corresponding International Application No. PCT/US2021/020796, dated Jun. 23, 2021, 10 pages.
Katzen et al. "Ethanol distillation: the fundamentals." Katzen International, Inc. 1999, pp. 269-288, Chapter 18.
Onuki et al. "Taking ethanol quality beyond fuel grade: A review." J. Inst. Brew. 2016; 122: 588-598.
Stout et al. "Preparation of Aldehyde-Free Ethyl Alcohol—Rapid Method." Analytical Edition, Mar. 15, 1933, pp. 100-101, vol. 5, No. 2.

*Primary Examiner* — Sikarl A Witherspoon

(57) ABSTRACT

The disclosure is directed to an apparatus and method for recovering ethanol from a fermentation broth. The fermentation broth comprises microbial biomass, ethanol, methanol, ethyl acetate, at least one thiol, and at least one compound having 3 or more carbon atoms. The method comprises separating at least microbial biomass from the fermentation broth to generate a process stream; removing, in any order, from the process stream: ethyl acetate by reacting ethyl acetate with a base compound followed by distillation; at least one thiol by adsorption or reaction to disulfide; methanol by distillation; compounds having 3 or more carbon atoms by distillation; and recovering ethanol by distillation; wherein the distillations may be conducted in a single column or two or more columns.

26 Claims, 3 Drawing Sheets

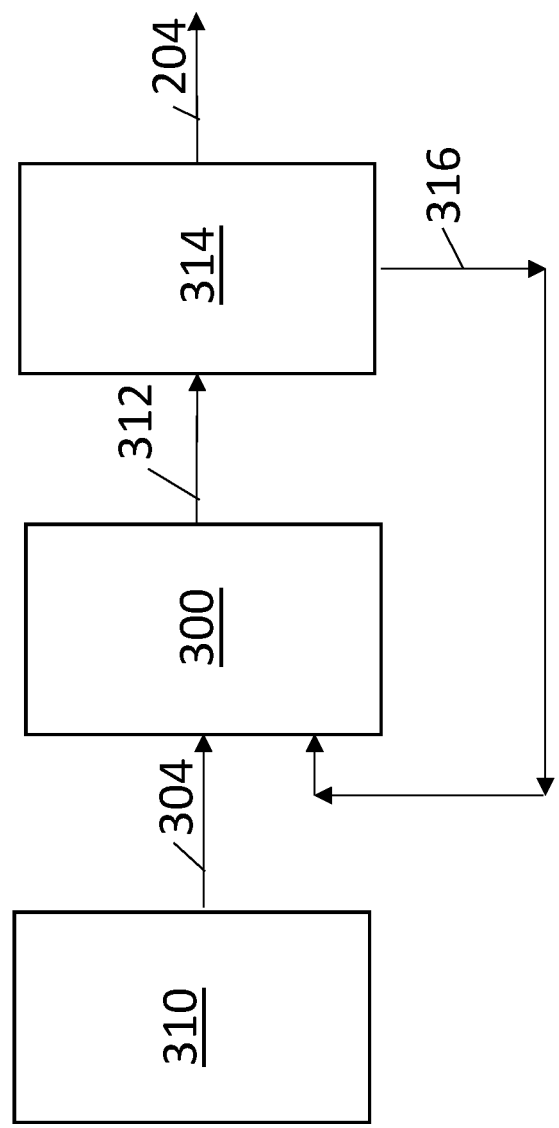

PROCESS FOR PURIFICATION OF PRODUCTS

CROSS REFERENCE TO RELATED APPLICATIONS

This application claims the benefit of U.S. Provisional Patent Application No. 62/988,176 filed Mar. 11, 2020, the entirety of which is incorporated herein by reference.

FIELD OF THE INVENTION

This invention relates to a method for recovering and purifying one or more products from a fermentation broth. In particular, the invention relates to the use of two or more separations to recover and purify products, such as ethanol, from a fermentation broth, where the fermentation broth contains microbial biomass, ethanol, and isopropanol.

BACKGROUND

Carbon dioxide ($CO_2$) accounts for about 76% of global greenhouse gas emissions from human activities, with methane (16%), nitrous oxide (6%), and fluorinated gases (2%) accounting for the balance (the United States Environmental Protection Agency). The majority of $CO_2$ comes from the burning of fossil fuels to produce energy, although industrial and forestry practices also emit $CO_2$ into the atmosphere. Reduction of greenhouse gas emissions, particularly $CO_2$, is critical to halting the progression of global warming and the accompanying shifts in climate and weather.

It has long been recognized that catalytic processes, such as the Fischer-Tropsch process, may be used to convert gases containing carbon dioxide ($CO_2$), carbon monoxide (CO), and/or hydrogen ($H_2$), such as industrial waste gas or syngas, into a variety of fuels and chemicals. Recently, however, gas fermentation has emerged as an alternative platform for the biological fixation of such gases. In particular, C1-fixing microorganisms have been demonstrated to convert gases containing $CO_2$, CO, and/or $H_2$ into products such as ethanol and isopropanol.

Typically, products produced through either Fischer-Tropsch and/or gas fermentation are separated through conventional distillation. The distillation process is based on the difference in the volatility, i.e., the difference in boiling point, of the components to be separated. By products produced and therefore present must also be separated from the product(s). However, for some end uses, simple conventional distillation without more has been shown to be unable to effectively separate the desired product from the solution at a high enough purity level.

For example, in gas fermentation using C1-fixing microorganisms, when ethanol is the desired products, by-products may be methanol, acetal, acetaldehyde, ethyl acetate, and possibly some sulfur containing compounds. Depending upon the end use of the ethanol, one or more of these by-products may be required to be removed to be below specified levels. To achieve a high purity product ethanol multiple separation steps may be required.

Accordingly, there remains a need for a system that is effective at separating by-product compounds from a gas fermentation product such as ethanol to achieve a high purity ethanol product.

BRIEF SUMMARY

The disclosure involves a method for recovering ethanol from a fermentation broth comprising microbial biomass, ethanol, methanol, ethyl acetate, at least one thiol, and at least one compound having 3 or more carbon atoms, the method comprising: separating at least microbial biomass from the fermentation broth to generate a process stream; removing, in any order, from the process stream: ethyl acetate by reacting ethyl acetate with a base compound followed by distillation; at least one thiol by adsorption or reaction to disulphide; methanol by distillation; compounds having 3 or more carbon atoms by distillation; and recovering ethanol by distillation; wherein the distillations may be conducted in a single column or two or more columns.

The fermentation broth may further comprise acetaldehyde and the method may further comprise removing the acetaldehyde, after removal of the microbial biomass to generate a process stream, by using a metal to reduce the acetaldehyde to an acetate followed by distillation.

The fermentation broth may further comprise at least one aldehyde and the method may further comprise removing the aldehyde, after removal of the microbial biomass to generate a process stream, by reducing to an alcohol. The reducing may be conducted using a reactive metal, amalgam, or a compound comprising a reactive metal. The reactive metal, amalgam, or compound may comprise zinc or aluminium. The reducing may be conducted by treatment with hydrazine. The aldehyde may be reduced to an alcohol as part of the step of removing ethyl acetate by reacting ethyl acetate with a base compound followed by distillation, see below.

The product ethanol may be recovered as part of the distillation steps where methanol is removed or where compounds having 3 or more carbon atoms are removed.

The method may be conducted where the steps of removing ethyl acetate by reacting ethyl acetate with a base compound followed by distillation and removing at least one thiol by adsorption or reaction to disulphide are performed prior to the steps of removing methanol by distillation and removing compounds having 3 or more carbon atoms by distillation.

The method may be conducted wherein the at least one distillation is conducted in an inert atmosphere or where all distillations are conducted in an inert atmosphere. The method may be conducted wherein the removing at least one thiol is in air or under an inert atmosphere.

The method may be conducted wherein the adsorption employs a strongly acidic cation exchange resin. The strongly acidic cation exchange resin may be Ag on a macro reticular polystyrene based ion exchange resin with strongly acidic sulfonic groups.

The fermentation broth may further comprise additional impurities and the method may further comprises treating the process stream with an adsorbent to remove the additional impurities. The adsorbent may be activated carbon, activated charcoal, or a strongly acidic cation exchange resin. The strongly acidic cation exchange resin may be Ag on a macro reticular polystyrene based ion exchange resin with strongly acidic sulfonic groups.

Another embodiment of the disclosure is directed to a method for separating ethanol from a fermentation broth comprising microbial biomass, ethanol, methanol, ethyl acetate, at least one thiol, and at least one compound having 3 or more carbon atoms, the method comprising: separating at least microbial biomass from the fermentation broth to generate a process stream depleted in microbial biomass; removing ethyl acetate from the process stream by reacting ethyl acetate with a base compound followed by distillation to generate an ethyl acetate-depleted stream; removing at least one thiol from the ethyl-acetate depleted stream by adsorption or reaction to disulphide to generate a thiol-depleted stream; and separating methanol, ethanol, and compounds having 3 or more carbon atoms from the thiol-depleted stream by distillation which may be conducted in a single column in two or more columns.

Yet another embodiment of the disclosure is directed to a method for separating ethanol from a fermentation broth comprising microbial biomass, ethanol, methanol, ethyl acetate, at least one thiol, and at least one compound having 3 or more carbon atoms, the method comprising separating at least microbial biomass from the fermentation broth to generate a process stream depleted in microbial biomass; removing at least one thiol from the process stream by adsorption or reaction to disulphide to generate a thiol-depleted stream; removing ethyl acetate from the thiol-depleted stream by reacting ethyl acetate with a base compound followed by distillation to generate an ethyl acetate-depleted stream; and separating methanol, ethanol, and compounds having 3 or more carbon atoms from the ethyl acetate-depleted stream by distillation which may be conducted in a single column or in two or more columns.

Still another embodiment of the disclosure is an apparatus for separating ethanol from a fermentation broth comprising microbial biomass, ethanol, methanol, ethyl acetate, at least one thiol, and at least one compound having 3 or more carbon atoms, the apparatus comprising: a first separation unit separating microbial biomass from the fermentation broth to generate a process stream comprising ethanol, methanol, ethyl acetate, at least one thiol, and at least one compound having 3 or more carbon atoms; a second separation unit removing, from the process stream, ethyl acetate by reacting ethyl acetate with a base compound followed by distillation; a third separation unit removing at least one thiol by adsorption or reaction to disulfide; and a distillation system to separate methanol, compounds having 3 or more carbon atoms and ethanol wherein the distillation system comprises a single column or two or more columns.

BRIEF DESCRIPTION OF THE DRAWINGS

FIG. 3 is a schematic process flow diagram showing the portion of an embodiment directed to the generation of the fermentation broth and the separation and removal of microbial biomass to generate the microbial biomass depleted process stream.

DETAILED DESCRIPTION

Figure 1:
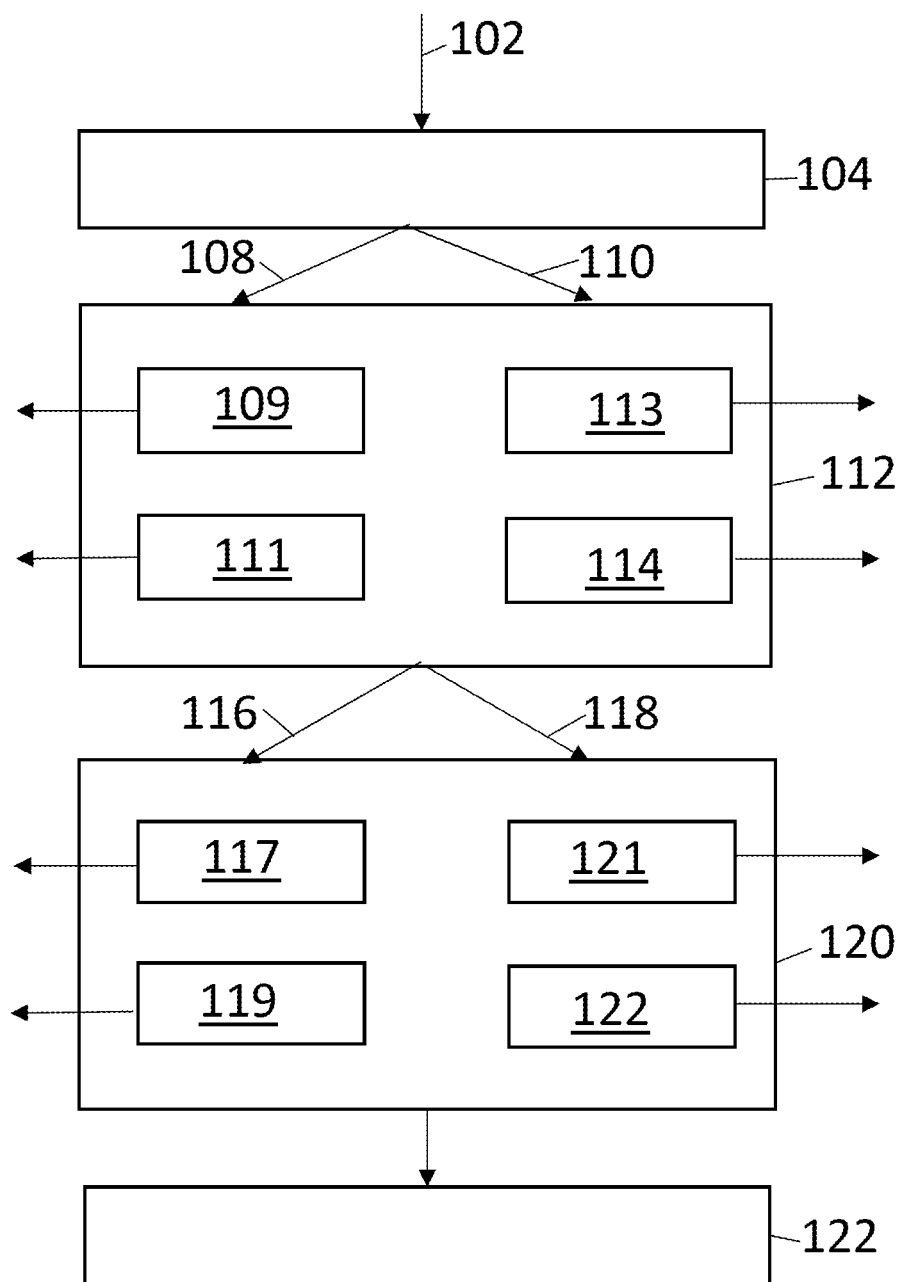
FIG. 1 shows a simplified series of separation steps in accordance with one embodiment of the disclosure, and particularly shows a useful order of the separation steps.

The invention provides a method for recovering product from a fermentation broth comprising microbial biomass, product, by-products, and impurities. The method allows for purification of the product for uses that require high purity product. For ease of understanding, the product will be described herein as ethanol. The ethanol is produced in a gas fermentation system using a biological catalyst and exits one or more bioreactors as part of a fermentation broth. The fermentation broth comprises microbial biomass, ethanol, and by-products such as methanol, ethyl acetate, at least one thiol, at least one compound having 3 or more carbon atoms, and possibly impurities. The fermentation broth may further comprise acetaldehyde. The fermentation broth may further comprise at least one aldehyde. The fermentation broth may additionally comprise impurities.

The substrate and/or C1-carbon source of the gas fermentation process may be a waste gas obtained as a byproduct of an industrial process or from another source, such as automobile exhaust fumes, biogas, or landfill gas or from electrolysis. The substrate and/or C1-carbon source may be syngas generated by pyrolysis, torrefaction, or gasification. In other words, waste material may be recycled by pyrolysis, torrefaction, or gasification to generate syngas which is used as the substrate and/or C1-carbon source.

In certain embodiments, the industrial process is selected from ferrous metal products manufacturing, such as a steel mill manufacturing, non-ferrous products manufacturing, petroleum refining, electric power production, carbon black production, paper and pulp manufacturing, ammonia production, methanol production, coke manufacturing, or any combination thereof. In these embodiments, the substrate and/or C1-carbon source may be captured from the industrial process before it is emitted into the atmosphere, using any known method.

The substrate and/or C1-carbon source may be syngas, such as syngas obtained by gasification of coal, gasification of refinery residues, gasification of biomass, gasification of lignocellulosic material, black liquor gasification, gasification of municipal solid waste, gasification of industrial solid waste, gasification of sewerage, gasification of sludge from wastewater treatment, reforming of natural gas, reforming of biogas, reforming of landfill gas or any combination thereof.

Examples of municipal solid waste include tires, plastics, and fibers in sholes, apparel, textiles. The municipal solid waste may be sorted or unsorted. Examples of biomass may include lignocellulosic material and may also include microbial biomass. Lignocellulosic material may include agriculture waste and forest waste.

The gas fermentation process of the substrate and/or C1-carbon source using a biocatalyst provides a fermentation broth containing the product and microbial biomass.

Microbial biomass is separated from the fermentation broth to generate a process stream depleted in microbial biomass. Generally, the process stream will comprise the product and some concentration of by-products and possibly impurities. For example, the process stream may comprise product ethanol as well as by products such as methanol, ethyl acetate, at least one thiol, and at least one compound having 3 or more carbon atoms. The process stream may also comprise acetaldehyde, and/or at least one aldehyde, and/or other impurities. The remainder of the fermentation broth comprises the microbial biomass which can be recycled to the bioreactors. The fermentation broth is typically an aqueous solution. The microbial biomass comprises at least one suitable microorganism used as the biocatalyst of the fermentation process. For example, the microorganism may be selected from *Escherichia coli, Saccharomyces cerevisiae, Clostridium acetobutylicum, Clostridium beijerinckii, Clostridium saccharbutyricum, Clostridium saccharoperbutylacetonicum, Clostridium butyricum, Clostridium diolis, Clostridium kluyveri, Clostridium pasterianium, Clostridium novyi, Clostridium difficile, Clostridium thermocellum, Clostridium cellulolyticum, Clostridium cellulovorans, Clostridium phytofermentans, Lactococcus lactis, Bacillus subtilis, Bacillus licheniformis, Zymomonas mobilis, Klebsiella oxytoca, Klebsiella pneumonia, Corynebacterium glutamicum, Trichoderma reesei, Cupriavidus necator, Pseudomonas putida, Lactobacillus plantarum*, and *Methylobacterium extorquens*. In certain instances, the microorganism may be a C1-fixing bacterium selected from

*Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides,* and *Thermoanaerobacter kiuvi.* In a specific embodiment, the microorganism is a member of the genus *Clostridium.* In certain instances, the microorganism is *Clostridium autoethanogenum.*

The microorganisms may be capable of producing a variety of different products. One or more products produced by the microorganisms may be a low boiling fermentation product. In certain instances, the product is ethanol, acetone, isopropanol, butanol, ketones, methyl ethyl ketone, acetone, 2-butanol, 1-propanol, methyl acetate, ethyl acetate, butanone, 1,3-butadiene, isoprene, isobutene, or any combination thereof. In certain embodiments, the method is optimized based upon the product being produced. In some embodiments, the product produced in the bioreactor is ethanol and isopropanol. The method may be optimized such that ethanol and isopropanol can be effectively removed from the fermentation broth. In some embodiments, the microorganism produces at least one by-product. In one embodiment the at least one by-product is acetic acid, lactic acid, acetone, 3-hydroxybutyrate, isobutanol, n-propanol, n-butanol, and/or 2,3-butanediol.

Known techniques for separating microbial biomass to generate the process stream comprising at least the product. For example, the fermentation broth may be passed from a bioreactor to a vacuum distillation vessel where the fermentation broth is partially vaporized to produce a product enriched stream comprising ethanol, and a product depleted stream comprising microbial biomass. Vacuum distillation is described in detail in, for example, US 2018/0264375.

Extractive distillation, either alone, or in combination with vacuum distillation is another known technique that may be used to separate a process stream depleted in microbial biomass from the fermentation broth. An extractive distillation agent works by interacting with a product to increase the relative volatility between the desired product and other components. For example, an extractive distillation agent has a high affinity for the desired product and a low affinity for the by-products. A proper extractive distillation agent should not form an azeotrope with components and should be capable of being separated from the product by a subsequent separation technique such as distillation. Suitable potential extractive distillation agents are listed, for example, in US 2020/0255362.

Another technique involves the use of a separator module adapted to receive fermentation broth from a bioreactor and to pass the broth through a filter to yield a retentate and a permeate. Often the permeate comprises at least the product and the retentate comprises the at least the microbial biomass of the fermentation broth, which may be recycled to the bioreactor. The filter may be a membrane, such as a cross-flow membrane or a hollow fiber membrane.

The process stream, separated from the fermentation broth and depleted in microbial biomass, comprises ethanol, methanol, ethyl acetate, at least one thiol, and at least one compound having 3 or more carbon atoms. The remainder of the fermentation broth may be recycled to the bioreactor, or maybe further treated and then recycled to the bioreactor. Ethanol for use in the fuel applications may not require a high degree of purity, but other applications of ethanol may require a high degree of purity to avoid unpleasant odor or flavors or concerns to human health. To produce the highest value ethanol, by-products commonly generated and found with the ethanol in the process stream need to be removed. Distillation is a primary technique to separate the desired ethanol, but distillation alone is not sufficient to achieve the necessary purity levels due to the similar temperature-vapor pressure profiles of the desired ethanol and the undesired by-products. Furthermore, in some situations, azeotropes may form making distillation difficult. Multiple separation techniques in multiple separation steps need to be combined to achieve the desired level of purity of the product ethanol. It is advantageous for specific separation steps to be conducted in a particular order to achieve the desired result.

Ethyl acetate may be present as a by-product in the process stream, and it is desirable to remove ethyl acetate from the process stream to generate a high purity ethanol product. Ethyl acetate is difficult to separate from ethanol. For example, ethyl acetate cannot be separated from ethanol by distillation or rectification because of the closeness of their boiling points. However, the present disclosure employs the alkaline hydrolysis of esters, or more specifically, the technique of hydrolysing the ethyl acetate with a base, such as sodium hydroxide, to form ethanol and acetic acid which is neutralized to an acetate, such as sodium acetate. The base is added at a location near to the feed of the process stream to the separation step. The base may be added above the location of the feed of the process stream into a column, such as for example, at a top or near to the top of the column. The base may be added to a reboiler feed, especially in batch operation. The resulting acetate is unreactive with ethanol, and the acetate is then readily separated from ethanol by distillation. Other bases are suitable for use in this separation step, and include bases such as potassium hydroxide, calcium hydroxide, lithium hydroxide, rubidium hydroxide, cesium hydroxide, barium hydroxide, ammonium hydroxide, magnesium hydroxide, and combinations thereof. In this separation step, ethyl acetate is removed from the process stream and hence from the product ethanol.

The process stream, now depleted in ethyl acetate, may then be treated with an adsorbent material to remove compounds containing sulfur such as a thiol. Sulfur containing compounds are known for imparting an unpleasant odor when makes the ethanol unsuitable for some high purity applications. Unpleasant odors may result from low levels of sulfur compounds, such as concentrations in the parts per billion range. Contacting the process stream comprising the at least one thiol with an adsorbent capable of adsorbing and thereby removing the thiol from the process stream will thereby remove the unpleasant odor from the stream as well. Suitable adsorbents include, for example, strongly acidic cation exchange resins. An example is a silver treated or impregnated neutralized strongly acidic ion exchange resin catalyst adsorbent. The resin may be a sulfonated styrene-divinyl benzene resin. Such synthetic resins are marketed under the name Amberlyst 15 from Rohm & Haas and LEWATIT SPC 118 from Bayer AG. A suitable adsorbent is marketed under the name Ag/Amberlyst-15 from Rohm & Haas. A suitable adsorbent is described in detail in U.S. Pat. No. 4,760,204. The treatment of the process stream may be operated in a continuous fashion, in a batch fashion, in a swing bed fashion, or in any other suitable mode of operation. The adsorbent may be arranged in a fixed bed, a moving bed, a fluidized, a simulated moving bed or in any other suitable arrangement.

In another embodiment, any mercaptans present could be oxidized using carbon to form disulfides in order to chemically convert the odorous mercaptans to non-odorous disulfides.

The treatment to remove sulfur compounds may be conducted in air or may be conducted in an inert atmosphere. Non limiting examples of inert atmosphere include a nitrogen atmosphere and a helium atmosphere. An advantage of using an inert atmosphere is the avoidance of producing undesired acetaldehyde. The adsorbent vessels may be purged with inert gas such as nitrogen and may be continuously purged with nitrogen.

The process stream, now depleted in both ethyl acetate and thiol, is distilled to separate ethanol, methanol, and at least one compound having 3 or more carbon atoms. The distillation may be accomplished in one, two, or more distillation columns. For example, a single distillation column may be used to separate the at least one compound having 3 or more carbon atoms as a bottoms stream from a methanol overhead stream and high purity ethanol side cut stream. In another embodiment, a first column may separate methanol as an overhead and a bottoms column with ethanol and at least one compound having 3 or more carbon atoms. In a second column, high purity ethanol is separated from the at least one compound having three or more carbon atoms.

One or more of the distillations may be conducted in an inert atmosphere. One or more of the distillation columns may be an extractive distillation column and employing an extractive distillation agent.

The fermentation process may produce fusel oils as a byproduct. The fermentation broth and the process stream depleted in microbial biomass may therefore further comprise fusel oils. Fusel oils may be removed from the process stream in the distillation step. In one embodiment, the fusel oils are removed as a side-draw from at least one of the distillation columns. As part of the same side-draw from at least one of the distillation columns, along with fusel oils, sulfur species may also be removed. Sulfur containing compounds that were not removed earlier in the process could be removed here.

The fermentation broth and the process stream may further comprise acetaldehyde. The acetaldehyde is an undesired component of the process stream and may be removed so as not to contaminate the product ethanol and reduce the purity of the product ethanol. This separation step is optional and may depend upon the amount of acetaldehyde present in the process stream. Acetaldehyde is removed from the process stream using a metal to reduce the acetaldehyde to an acetate followed by distillation to remove the acetate. The acetate formed may be ethyl acetate. Therefore, the acetaldehyde may be removed in the same step as the removal of ethyl acetate.

The fermentation broth and the process stream may further comprise an aldehyde. The aldehyde is an undesired component of the process stream and should be removed so as not to contaminate the product ethanol and reduce the purity of the product ethanol. The aldehyde may be reduced to an alcohol and then removed from the process stream. The reduction of the aldehyde may be accomplished using a reactive metal, amalgam or a compound comprising a reactive metal. Suitable metals, amalgams and compounds may comprise zinc or aluminium. Mixtures of different metals, amalgams and compounds may be used. In another embodiment, the process stream may be treated with hydrazine to react with the aldehyde and form an alkane. The alcohol produced or the alkane produced may be removed in the distillation step(s) so that the ethanol is recovered at a high purity.

The fermentation broth and the process stream may further comprise undesirable impurities. The process stream may be treated using an adsorbent to remove impurities. Suitable adsorbents include activated carbon, activated charcoal, and silver treated or impregnated neutralized strongly acidic ion exchange resin catalyst adsorbent such as that marketed under the name Ag/Amberlyst-15. The process stream may be treated to remove impurities at any point in the process. In one embodiment, the process stream is treated to remove impurities before other separation steps. In another embodiment, the process stream is treated to remove impurities in the same step as the removing at least one thiol.

The separation steps may be performed in any order, but there are advantages to performing the steps in a certain order. It is advantageous to remove the ethyl acetate and the thiol from the process stream before the methanol and the compound having 3 or more carbon atoms. In one embodiment, the ethyl acetate is removed from the process stream first.

Optionally, the purified ethanol stream may be dried or dehydrated. Because ethanol forms azeotropes with water, simple distillation can dehydrate ethanol up to about 90 wt %, but removing the remaining water requires another technique. Such techniques are known, and suitable techniques include the use of membrane dehydration and adsorbent dehydration. Example membranes techniques include membrane vapor permeation or pervaporation modes. Multiple different membrane are commercially available for the dehydration of ethanol. Adsorption, and pressure swing absorption (PSA), are techniques known to produce anhydrous ethanol. Many zeolitic adsorbents are commercially available for use in PSA systems.

FIG. 1 shows a process flow where microbial biomass is removed from fermentation broth 102 in step 104 to form a process stream depleted in microbial biomass. The process stream is passed to either sequence 108 or sequence 110 of separation step 112. In sequence 108 of separation step 112, first ethyl acetate is removed by reacting ethyl acetate with a base compound followed by distillation in 109 and then at least one thiol is separated by adsorption or reaction to disulfide in 111. In sequence 110 of separation step 112, first at least one thiol is separated by adsorption or reaction to disulfide in 113 and then ethyl acetate is removed by reacting ethyl acetate with a base compound followed by distillation in 114. After separation step 112, the process stream is depleted in ethyl acetate and thiol and is passed to sequence 116 or sequence 118 of separation step 120. In sequence 116 of separation step 120, first methanol is separated by distillation in 117 and then at least one compound having 3 or more carbon atoms is separated by distillation in 119. In sequence 118 of separation step 120, first at least one compound having 3 or more carbon atoms is separated by distillation in 121 and then methanol is separated by distillation in 122. Ethanol is then recovered in step 122.

Figure 2:
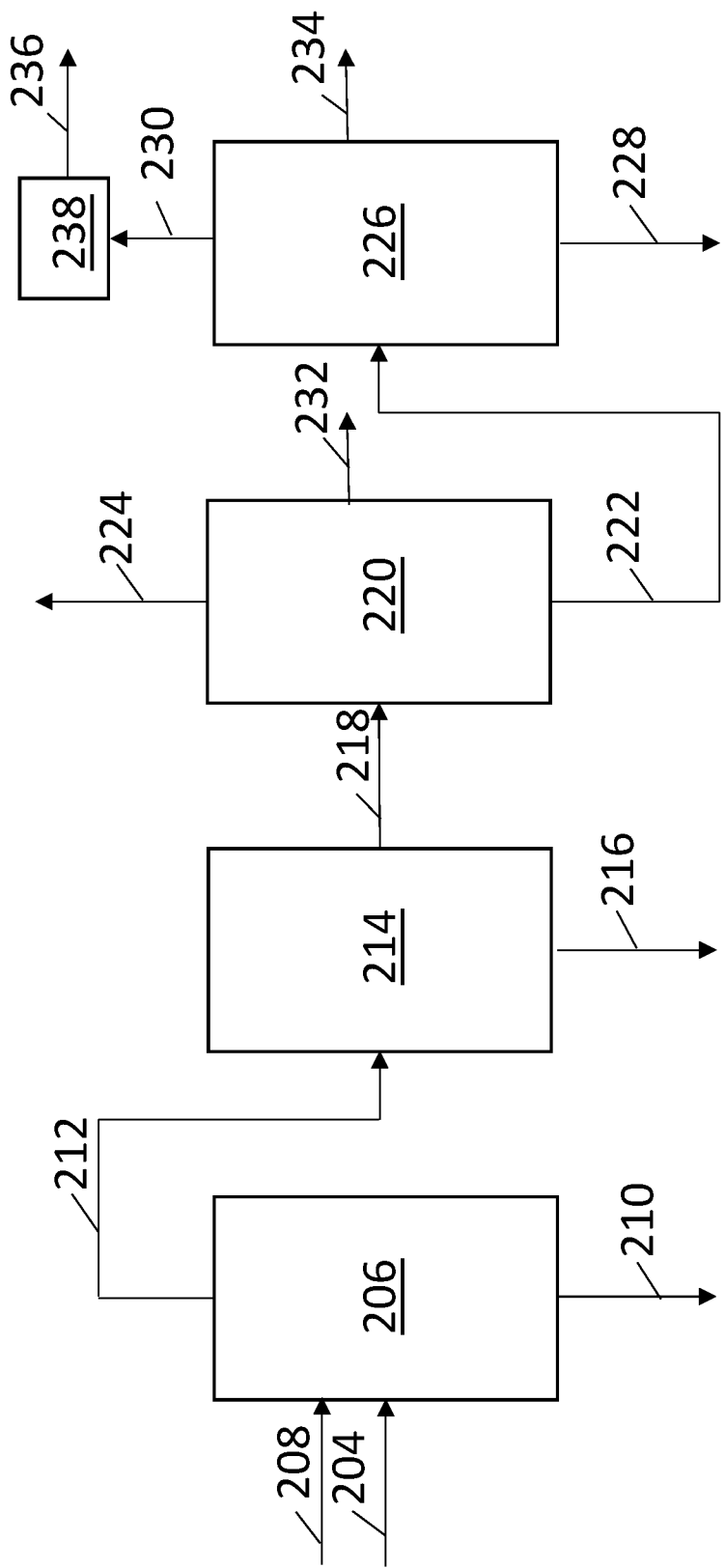
FIG. 2 is a schematic process flow diagram showing one embodiment of the disclosure.

FIG. 2 shows one embodiment of the disclosure where the separation steps are arranged in a particular order. A process stream that has already been separated from fermentation broth and comprises ethyl acetate, at least one thiol, methanol, at least one compound having 3 or more carbon atoms and ethanol is conducted in line 204 and introduced to vessel 206 where ethyl acetate is removed. Base, such as sodium hydroxide, is introduced to vessel 206 in line 208. The base reacts with ethyl acetate to form sodium acetate which removed in line 210. The ethyl acetate-depleted process stream is passed from vessel 206 to vessel 214 via line 212. Vessel 214 houses an adsorbent capable of adsorbing at least one thiol. The process stream depleted in ethyl-acetate and thiol is passed from vessel 214 to vessel 220 in line 218. At some point in the process the thiol adsorbed by the adsorbent is desorbed in a desorption step and removed via line 216. Vessel 220 is a distillation column where methanol is removed as an overhead in line 224, and the bottoms in line 222 containing ethanol and at least one compound having 3 or more carbon atoms is passed to vessel 226. Optional side-draw 232 is also shown where fusel oils and/or sulfur containing compounds may be withdrawn. Vessel 226 is a distillation column where the at least one compound having 3 or more carbon atoms is removed in bottoms stream 228. Optional side-draw 234 is also shown where fusel oils and/or sulfur containing compounds may be withdrawn. Purified ethanol is removed in overhead line 230. Optionally, purified ethanol in line 230 may be dried in ethanol dehydration unit 238 to provide purified dehydrated ethanol in line 236. Ethanol dehydration unit 238 may be a membrane system or a PSA.

FIG. 3 Shows the portion of the embodiment of the generation of the fermentation broth and the separation and removal of microbial biomass to generate the microbial biomass depleted process stream. Industrial process or gasification unit 310 provides substrate in conduit 304 which is passed into bioreactor 300 where it is fermented using a microorganism to produce the target product such as ethanol. Fermentation broth 312 comprising microbial biomass, ethyl acetate, at least one thiol, methanol, at least one compound having 3 or more carbon atoms and ethanol is removed from bioreactor 300 and passed to separator 314 where microbial biomass is separated into line 316 and recycled to bioreactor 300. Process stream 204, depleted in microbial biomass, comprises ethyl acetate, at least one thiol, methanol, at least one compound having 3 or more carbon atoms and ethanol, is ready for purification as described in FIG. 2.

The invention claimed is:

1. A method for recovering ethanol from a fermentation broth comprising microbial biomass, ethanol, methanol, ethyl acetate, at least one thiol, and at least one compound having 3 or more carbon atoms, the method comprising:
   a. separating at least microbial biomass from the fermentation broth to generate a process stream comprising ethanol, methanol, ethyl acetate, at least one thiol, and at least one compound having 3 or more carbon atoms;
   b. removing, in any order, from the process stream:
      i. ethyl acetate by reacting ethyl acetate with a base compound followed by distillation;
      ii. at least one thiol by adsorption or reaction to disulphide;
      iii. methanol by distillation;
      iv. compounds having 3 or more carbon atoms by distillation; and
   c. recovering ethanol by distillation wherein the distillations may be conducted in a single column or two or more columns.

2. The method of claim 1 where in the fermentation broth and the process stream further comprise acetaldehyde and the method further comprises removing the acetaldehyde from the process stream using a metal to reduce the acetaldehyde to an acetate followed by distillation.

3. The method of claim 1 where in the fermentation broth and the process stream further comprise at least one aldehyde and the method further comprises removing the aldehyde in step b. by reducing the aldehyde to an alcohol or reacting the aldehyde to form an alkane.

4. The method of claim 3 wherein the reducing to an alcohol is conducted using a reactive metal, amalgam, or a compound comprising a reactive metal.

5. The method of claim 4 wherein the reactive metal, amalgam, or compound comprises zinc or aluminium.

6. The method of claim 3 wherein the reacting to form an alkane is conducted by treatment with hydrazine.

7. The method of claim 3 wherein the removing at least one aldehyde is part of step b sub-step i.

8. The method of claim 1 wherein the ethanol is removed as part of the distillation of step b sub-step iii. or step b sub-step iv.

9. The method of claim 1 wherein in step b sub-steps i. and ii. are conducted before sub-steps iii. and iv.

10. The method of claim 1 wherein the at least one distillation is conducted in an inert atmosphere.

11. The method of claim 1 wherein all distillations are conducted in an inert atmosphere.

12. The method of claim 1 wherein the removing at least one thiol is conducted in air or under an inert atmosphere.

13. The method of claim 1 wherein the adsorption employs a strongly acidic cation exchange resin.

14. The method of claim 13 wherein the strongly acidic cation exchange resin is Ag on a macro reticular polystyrene based ion exchange resin with strongly acidic sulfonic groups.

15. The method of claim 1 wherein the fermentation broth and the process stream further comprise impurities and the method further comprises treating the process stream with an adsorbent to remove impurities.

16. The method of claim 15 wherein the adsorbent is activated carbon, activated charcoal, or a strongly acidic cation exchange resin.

17. The method of claim 16 wherein the strongly acidic cation exchange resin is Ag on a macro reticular polystyrene based ion exchange resin with strongly acidic sulfonic groups.

18. The method of claim 1 further comprising removing fusel oil by the distillation in step b iii., in step c, or in both step b iii. and step c.

19. The method of claim 1 further comprising removing at least one sulfur containing compound by the distillation in step b iii., in step c, or in both step b iii. and step c.

20. The method of claim 1 further comprising fermenting an industrial waste gas or a syngas from a gasification process using a microorganism to generate the fermentation broth.

21. A method for separating ethanol from a fermentation broth comprising microbial biomass, ethanol, methanol, ethyl acetate, at least one thiol, and at least one compound having 3 or more carbon atoms, the method comprising:
   a. separating at least microbial biomass from the fermentation broth to generate a process stream comprising ethanol, methanol, ethyl acetate, at least one thiol, and at least one compound having 3 or more carbon atoms;
   b. removing ethyl acetate from the process stream by reacting ethyl acetate with a base compound followed by distillation to generate an ethyl acetate-depleted stream;
   c. removing at least one thiol from the ethyl-acetate depleted stream by adsorption or reaction to disulphide to generate a thiol-depleted stream; and
   d. separating methanol, ethanol, and compounds having 3 or more carbon atoms from the thiol-depleted stream by distillation, wherein the distillation may be conducted in a single column or in two or more columns.

22. A method for separating ethanol from a fermentation broth comprising microbial biomass, ethanol, methanol, ethyl acetate, at least one thiol, and at least one compound having 3 or more carbon atoms the method comprising:
  a. separating at least microbial biomass from the fermentation broth to generate a process stream comprising ethanol, methanol, ethyl acetate, at least one thiol, and at least one compound having 3 or more carbon atoms;
  b. removing at least one thiol from the process stream by adsorption or reaction to disulphide to generate a thiol-depleted stream;
  c. removing ethyl acetate from the thiol-depleted stream by reacting ethyl acetate with a base compound followed by distillation to generate an ethyl acetate-depleted stream; and
  d. separating methanol, ethanol, and compounds having 3 or more carbon atoms from the ethyl acetate-depleted stream by distillation, wherein the distillation may be conducted in a single column or in two or more columns.

23. An apparatus for separating ethanol from a fermentation broth comprising microbial biomass, ethanol, methanol, ethyl acetate, at least one thiol, and at least one compound having 3 or more carbon atoms, the apparatus comprising:
  a. a first separation unit, in fluid communication with a bioreactor, configured to separate at least microbial biomass from the fermentation broth and generate a process stream comprising ethanol, methanol, ethyl acetate, at least one thiol, and at least one compound having 3 or more carbon atoms;
  b. a second separation unit, in fluid communication with the first separation unit, in fluid communication with a base compound conduit, and configured to remove ethyl acetate from the process stream by reacting the ethyl acetate with a base compound followed by distillation;
  c. a third separation unit in fluid communication with the second separation unit, and in fluid communication with a sulfur-containing compound conduit, and configured to remove at least one thiol by adsorption or reaction to disulfide; and
  d. a distillation system in fluid communication with the third separation unit, and configured to separate methanol, compounds having 3 or more carbon atoms and ethanol wherein the distillation system comprises a single column or two or more columns, and is in fluid communication with a methanol conduit, a C3+ conduit, and an ethanol conduit.

24. The apparatus of claim 23 further comprising a dehydration unit in fluid communication with the ethanol conduit.

25. The apparatus of claim 23 further comprising at least one side-draw in fluid communication with the distillation system.

26. The apparatus of claim 23 wherein the bioreactor is in fluid communication with a substrate conduit, the substrate conduit in fluid communication with an industrial process or a gasification process.

* * * * *